United States Patent [19]

Martyn

[11] Patent Number: 5,450,744
[45] Date of Patent: Sep. 19, 1995

[54] CONTAMINATION MONITORING SYSTEM

[75] Inventor: Richard S. Martyn, East Fremantle, Australia

[73] Assignee: Senson Limited, Australia

[21] Appl. No.: 305,726

[22] Filed: Sep. 14, 1994

[30] Foreign Application Priority Data

Sep. 14, 1993 [AU]  Australia ................. PM1208

[51] Int. Cl.⁶ .............. G01N 27/06; B01D 35/143; G08B 21/00
[52] U.S. Cl. .................. 73/61.71; 73/61.42; 324/453; 340/609
[58] Field of Search ............ 73/61.71, 61.42; 324/71.4, 453; 340/603, 607, 609

[56] References Cited

U.S. PATENT DOCUMENTS

| | | | |
|---|---|---|---|
| 3,238,452 | 3/1966 | Schmitt et al. | 73/61.71 |
| 3,611,790 | 10/1971 | Brouwer et al. | 73/61.71 |
| 3,635,082 | 1/1972 | Prellwitz et al. | 73/194 M |
| 3,831,083 | 8/1974 | Teass, Jr. et al. | 324/30 R |
| 3,990,066 | 11/1976 | Malmgren | 340/285 |
| 4,028,618 | 6/1977 | Teass, Jr. | 324/30 R |
| 4,392,110 | 7/1983 | El-Menshawy et al. | 324/453 |
| 4,937,557 | 6/1990 | Tucci et al. | 340/603 |
| 5,041,856 | 8/1991 | Veronesi et al. | 324/204 |
| 5,145,575 | 9/1992 | Burrows | 210/85 |
| 5,298,161 | 3/1994 | Sieg | 210/321.78 |

FOREIGN PATENT DOCUMENTS

| | | | |
|---|---|---|---|
| 62-76440 | 4/1987 | Japan | 324/71.4 |
| 0746268 | 7/1980 | U.S.S.R. | 73/61.71 |
| 0972378 | 11/1982 | U.S.S.R. | 324/71.4 |

*Primary Examiner*—Hezron E. Williams
*Assistant Examiner*—J. David Wiggins
*Attorney, Agent, or Firm*—Gipple & Hale

[57] ABSTRACT

A contamination monitoring system for monitoring contaminants in a liquid, comprising a first electrical conductivity sensor, a second electrical conductivity sensor, a filter and a pump, the filter being disposed between the first sensor and the second sensor, the pump being arranged to circulate the liquid, the first electrical conductivity sensor providing an indication of dissolved ionic contamination levels in the liquid prior to filtration of the liquid by the filter, the second electrical conductivity sensor providing an indication of dissolved ionic contamination levels in the liquid after filtering the liquid by the filter, the conductivity measured by the second electrical conductivity sensor being compared against a value to determine whether the liquid should be retained or discarded.

8 Claims, 1 Drawing Sheet

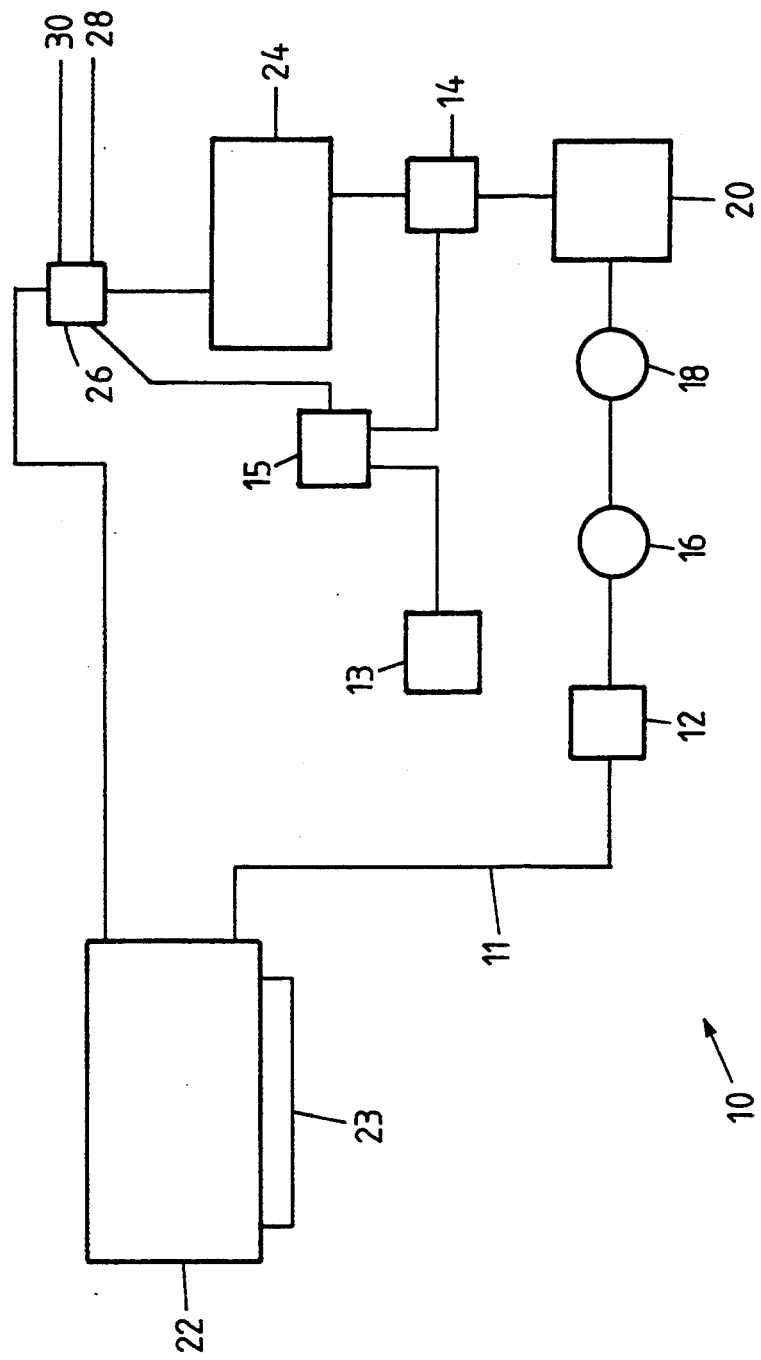

CONTAMINATION MONITORING SYSTEM

BACKGROUND OF THE INVENTION

The present invention relates to a contamination monitoring system. In particular, the present invention relates to a contamination monitoring system for monitoring contamination levels of dissolved ions in liquids. Contamination monitoring has wide applications in the areas of process control and quality control.

An example of where a contamination monitoring system is applicable is in the electronics industry, in particular cleaning of printed circuit boards. Printed circuit boards are typically cleaned by immersing them in a cleaning solution to remove any unwanted matter. The unwanted matter is typically dissolved into the cleaning solution and consequently, the cleaning solution ultimately becomes contaminated. If the contamination level of the cleaning solution is not monitored, then contaminants from one batch of printed circuit boards could be transferred to the next batch of printed circuit boards to be cleaned. Further, relatively uncontaminated cleaning liquids could be discarded unnecessarily, representing a financial loss. Therefore, there is a need for a system which provides monitoring of contamination levels in liquids for such application.

BRIEF SUMMARY OF THE INVENTION

In accordance with one aspect of the present invention, there is provided a contamination monitoring system for monitoring contaminants in a liquid, comprising a liquid flow path provided with a first sensor, a second sensor, a filter means and a pump means, the filter means being disposed between the first sensor and the second sensor, the pump means being arranged to pump the liquid along the flow path, the first sensor providing an indication of contamination levels in the liquid prior to filtration of the liquid by the filtering means, the second sensor providing an indication of contamination levels in the liquid after filtering of the liquid by the filter means.

It should be appreciated that the present invention is applicable in a large range of situations. The embodiment described below relates to cleaning printed circuit boards, however the present invention is not specifically limited thereto.

BRIEF DESCRIPTION OF THE DRAWINGS

The present invention will now be described, by way of example, with reference to the accompanying drawing which is a block diagram of a contamination monitoring system in accordance with the present invention.

DETAILED DESCRIPTION

Shown in the accompanying drawing, is a contamination monitoring system 10 comprising a liquid flow path provided with a first sensor 12, a second sensor 14, a first filter 16, a second filter 18 and a pump 20. The pump 20 pumps a liquid to be monitored along the liquid flow path 11 through the contamination monitoring system 10. In this embodiment the liquid flow path 11 completes a circuit although this is not essential. The filters 16 and 18 are provided between the sensors 12 senses and 14 such that the sensor 12 sensors contamination in the liquid prior to filtration and the sensor 14 senses contamination in the liquid after passing through the filters 16 and 18.

The contamination monitoring system 10 shown in FIG. 1 is arranged to be used in printed circuit board cleaning in electronics industry. Typically, printed circuit board cleaning is done by an ultrasonic cleaner. Printed circuit boards to be cleaned are immersed in a cleaning liquid and agitated by ultrasound. To further enhance the cleaning ability of the ultrasonic cleaner, the cleaning liquid is typically a solvent or aqueous cleaner. As the printed circuit boards are cleaned, contaminants are passed into the cleaning liquid. Such contaminants include physical particles and organic contaminants. Typically, many of the contaminants are in the form of dissolved ions in the cleaning liquid.

In the accompanying drawing, there is also shown a cleaning tank 22 of an ultrasonic cleaner having an ultrasonic vibrator 23, a radiator or heat exchanger 24 and a bypass solenoid 26 having a primary inlet and a primary outlet. The cleaning tank 22 contains a cleaning liquid into which printed circuit boards to be cleaned are immersed. The radiator 24 is provided to cool the cleaning liquid as it passes through the contamination monitoring system 10, since the cleaning liquid may become heated as a result of ultrasonic agitation.

The bypass solenoid 26 is provided to allow cleaning liquid which is overly contaminated to be removed through a secondary outlet 28 and for fresh cleaning liquid to replace any removed liquid via a secondary inlet 30.

Since contaminants in the cleaning liquid after removal of physical particles are principally in the form of dissolved ions, it is convenient for the sensors 12 and 14 to measure the electrical conductivity of the cleaning liquid to determine contamination levels. Further, the filter 16 is preferably a mesh filter to remove particulate contaminants. The filter 18 is preferably an activated carbon filter to remove organic contaminants. It should be noted that other types and quantities of filters may be provided depending upon the application for which the contamination monitoring system 10 is intended to be used. For example, in environments where the liquid has a large amount of particulate contaminants, it may be desirable to add a pre-filter to remove large particles from the liquid. The pre-filter may be disposed before the filter 16, and in some instances, before the sensor 12. There is also provided a number of preset values 13 and a comparator 15. The comparator 15 is arranged to compare values from the preset values 13 and the sensor 14. The comparator 15 controls the bypass solenoid 26 according to comparison results. In use, the cleaning liquid is circulated by the pump 20 from the cleaning tank 22 through the contamination monitoring system 10 and returned to the cleaning tank 22 of the ultrasonic cleaner. The cleaning liquid passes firstly through the sensor 12 which determines the conductivity of the cleaning liquid prior to filtration. The cleaning liquid is then passed through the filters 16 and 18 which filter contaminants from the cleaning liquid. The filtered cleaning liquid passes through the sensor 14 which determines the conductivity of the filtered cleaning liquid.

The radiator 24 cools the filtered cleaning liquid, which helps increase efficiency of the ultrasonic cleaner and also reduces flammability of the filtered cleaning liquid. Under normal operating conditions, the filtered cleaning liquid passes from the radiator 24 through the bypass solenoid 26 and is returned to the cleaning tank 22 for re-use.

Information received from the sensors 12 and 14 can be used to determine a variety of information about the cleaning liquid and the contamination monitoring system 10. If, for example, the sensor 12 senses that the conductivity of the cleaning liquid indicates a level of contaminants and further that the sensor 14 determines that the conductivity of the filtered cleaning liquid indicates the same level of contaminants, then the filters 16 and 18 need replacing.

Further, the difference in conductivity measured by the sensors 12 and 14 can be used to determine the cleanliness of printed circuit boards within the cleaning tank 22. When printed circuit boards are initially placed into the cleaning tank 22 and cleaning is commenced, there is typically a large difference in the conductivity measured by sensor 12 compared with the lower conductivity measured by sensor 14. As cleaning continues, typically the conductivity measured by sensors 12 and 14 increases as the batch of printed circuit boards within the cleaning tank 22 is cleaned. Therefore, a levelling off effect is seen in the difference between the conductivities measured by the sensors 12 and 14. This levelling off effect can be used to determine when printed circuit boards within the cleaning tank 22 are cleaned and may be removed.

Since the conductivity of the filtered cleaning liquid measured by the sensor 14 represents the amount of contaminants being returned to the cleaning tank 22, this value can be used to maintain the cleanliness of the cleaning liquid. If the conductivity measured by the sensor 14 indicates that the filtered cleaning liquid has a degree of contamination which exceeds a desired level, which indication is a result of the comparator 15 comparing the conductivity from the sensor 14 with the preset value 13, the bypass solenoid 16 is activated by the comparator 15. When the bypass solenoid 26 is in the activated state, the cleaning liquid from the radiator 24 is not returned to the cleaning tank 22, but is redirected to the outlet 28. Typically, the outlet 28 leads to a storage container, so that the dirty cleaning liquid can be recycled or reprocessed. Further, in the activated state, the bypass solenoid 26 allows fresh cleaning liquid present at the inlet 30 to be released into the cleaning tank 22. Thus, the preset value 13, the comparator 15 and the bypass solenoid 26 act as a flow control means.

Replacement of the dirty cleaning liquid can occur in one of two ways. Firstly, the entire batch of dirty cleaning liquid in the cleaning tank 22 can be replaced with fresh cleaning liquid. Alternatively, the dirty cleaning liquid can be replaced on a continuous or "trickle" basis with fresh cleaning liquid until contaminants in the cleaning liquid have decreased to an acceptable level.

In this instance, the inlet 30 is typically connected to a liquid supply means in the form of a storage tank in which fresh cleaning liquid is stored. It is envisaged that a second pump may be necessary to pump fresh cleaning liquid from the storage tank through the inlet 30 to the cleaning tank 22. There may also be provided a level indicator in the cleaning tank 22 so that the level of cleaning liquid therein may be determined. The provision of a level indicator would prevent loss of cleaning liquid by more liquid being removed through the outlet 28 than added through the inlet 30. The level indicator also allows regulation of the volume of cleaning liquid depending upon the number of printed circuit boards to be cleaned. When the sensor 14 indicates that the contaminant level within the cleaning liquid has dropped to a sufficiently low level, which indication is again performed by comparison with the preset value 13 by the comparator 15, the bypass solenoid 26 is deactivated by the comparator 15. In the deactivated state of the solenoid 26, cleaning liquid from the radiator 24 is returned to the cleaning tank 22.

It is envisaged that the preset values 13, which are compared with the conductivity measured by the sensor 14 to determine whether the liquid has an unacceptably high contamination level, may be calibrated to conform to Australian Standard 3508.3 (1990), or other industry standards. Further, a number of predetermined settings may be provided so that, for example, military specification, industry specification and low grade specification may be selected by use of a switch or some other convenient means. Further, it is envisaged that information from the sensors 12 and 14 may be output to a computer, for example by a RS-232 serial interface. Such an interface would allow analysis of the information, for example to compare different cleaning liquids or filters, or for a comparison to be made between previous information and present information to determine such things as efficiency and the amount of cleaning liquid used. A long term history analysis may be performed to allow simulations and modelling to be conducted, and also to determine any sources of contamination.

It should be apparent to a person skilled in the art that the present invention has applications in a variety of fields other than printed circuit board cleaning and the present invention is not taken to be limited thereto.

Modifications and variations such as would be deemed apparent to a skilled addressee are deemed within the scope of the present invention.

I claim:

1. A contamination monitoring system for monitoring contaminants in a liquid, comprising a liquid flow path provided with a first sensor, a second sensor, a filter means and a pump means, the filter means being disposed between the first sensor and the second sensor, the pump means being arranged to pump the liquid along the flow path, the first sensor providing an indication of contamination levels in the liquid prior to filtration of the liquid by the filter means and the second sensor providing an indication of contamination level in the liquid after filtration of the liquid by the filter means, wherein the contamination monitoring system further comprises a flow control means including a primary inlet and a primary outlet, the flow control means being disposed after the second sensor, wherein under normal operation conditions, the liquid flows through the flow control means from the primary inlet to the primary outlet, and wherein the flow control means further comprises a secondary inlet and a secondary outlet, whereby if the second sensor indicates an unacceptable level of contaminants in the liquid, the flow control means is activated such that the liquid is redirected from the primary outlet to the secondary outlet, the secondary inlet being redirected to the primary outlet, a liquid supply means connected to the secondary inlet providing liquid to replace the redirected liquid.

2. A contamination monitoring system for monitoring contaminants in a liquid, comprising a liquid flow path provided with a first sensor, a second sensor, a filter means and a pump means, the filter means being disposed between the first sensor and the second sensor, the pump means being arranged to pump the liquid along the flow path, the first sensor providing an indication of contamination levels in the liquid prior to filtration of the liquid by the filter means and the second sensor providing an indication of contamination level in the liquid after filtration of the liquid by the filter means, wherein the contamination monitoring system further comprises a heat exchange means located in the liquid flow path, the heat exchange means being arranged so as to cool the liquid.

3. A contamination monitoring system for monitoring contaminants in a liquid, comprising a liquid flow path provided with a first sensor, a second sensor, a filter means and a pump means, the filter means being disposed between the first sensor and the second sensor, the pump means being arranged to pump the liquid along the flow path, the first sensor providing an indication of contamination levels in the liquid prior to filtration of the liquid by the filter means and the second sensor providing an indication of contamination level in the liquid after filtration of the liquid by the filter means, wherein the filter means comprises a mesh filter and an activated carbon filter, where the two distinct, separate filters are arranged in series, one before the other, within the liquid flow path that passes through each filter.

4. A contamination monitoring system according to claim 1, wherein the first sensor and the second sensor are electrical conductivity sensors.

5. A contamination monitoring system according to claim 1, wherein the contamination monitoring system further comprises a heat exchange means located in the liquid flow path, the heat exchange means being arranged so as to cool the liquid.

6. A contamination monitoring system according to claim 1, wherein the liquid supply means includes a second pump means arranged to pump liquid from the liquid supply means to the secondary inlet.

7. A contamination monitoring system according to claim 1, wherein the filter means comprises a mesh filter and an activated carbon filter where the two distinct, separate filters are arranged in series, one before the other, within the liquid flow path that passes through each filter.

8. A contamination monitoring system according to claim 1, in which the liquid flow path is in the form of a closed hydraulic circuit.

* * * * *